United States Patent [19]
Deen et al.

[11] 4,282,108
[45] Aug. 4, 1981

[54] OIL-SOLUBLE SPIRO-[CYCLOALKANE-OXAZOLIDINES], THEIR PREPARATION AND USE AS ADDITIVES AND CHELATING AGENTS FOR FUNCTIONAL FLUIDS

[75] Inventors: Harold E. Deen, Cranford; Esther D. Winans, Colonia; Jack Ryer, East Brunswick; Rosemary O'Halloran, Union, all of N.J.

[73] Assignee: Exxon Research & Engineering Co., Florham Park, N.J.

[21] Appl. No.: 110,004

[22] Filed: Jan. 7, 1980

[51] Int. Cl.$^3$ .......................... C10M 1/32; C10M 3/26
[52] U.S. Cl. ............................ 252/51.5 R; 252/515 A
[58] Field of Search .............. 256/51.5 A; 252/51.5 R

[56]  References Cited
U.S. PATENT DOCUMENTS

| 3,632,511 | 1/1972 | Liao | 252/51.5 A |
|---|---|---|---|
| 3,679,428 | 7/1972 | Shiba et al. | 96/124 |
| 3,738,992 | 6/1973 | Frump | 252/51.5 A X |
| 3,843,726 | 10/1974 | Cobb | 260/570.5 S |
| 4,017,406 | 4/1977 | Brois et al. | 252/51.5 A |
| 4,049,564 | 9/1977 | Ryer et al. | 252/51.5 A |
| 4,062,786 | 12/1977 | Brois et al. | 252/51.5 R |
| 4,070,370 | 1/1978 | Elliott et al. | 260/326.25 |

FOREIGN PATENT DOCUMENTS 564506 10/1944 United Kingdom .
809001 2/1959 United Kingdom .
984409 2/1965 United Kingdom .

OTHER PUBLICATIONS

"Chemistry and Use of Aminohydroxy Compounds", Commercial Solvents Corp., N. Y.
Senkus, "J.A.C.S.", 67, p. 1515, 1945.
Bergmann, "Chem. Rev.", 53, p. 309, 1953.
Hancock et al., "J.A.C.S.", 66, p. 1747, 1944.

Primary Examiner—Paul F. Shaver
Attorney, Agent, or Firm—R. A. Dexter; J. J. Mahon

[57] ABSTRACT

Oil-soluble spiro-[cycloalkane-oxazolidines], e.g. spiro-[cyclopentane-1,2-(4'-ethyl-4'-methylol)-oxazolidines-1', 3'] which are the reaction products of a cycloalkanone and an amino-propane monool or diol are additives which feature activity in functional fluids, e.g. mineral oil base automatic transmission fluids, as copper corrosion inhibitors and as chelating agents.

6 Claims, No Drawings

OIL-SOLUBLE SPIRO-[CYCLOALKANE-OXAZOLIDINES], THEIR PREPARATION AND USE AS ADDITIVES AND CHELATING AGENTS FOR FUNCTIONAL FLUIDS

BACKGROUND OF THE INVENTION

1. Field of the Invention

The invention relates to oil-soluble spiro [cycloalkane-oxazolidines], e.g. spiro-[cyclopentane-1,2'-(4'-ethyl-4'methylol)-oxazolidine-1',3'] particularly those substituted in the 2 position with a spiro cycloalkane group containing from 5 to 12 carbon atoms, which oxazolidines are derived from the reaction of a cycloalkanone and amino-alkane diol or aminoalkanol.

These oil-soluble adducts have utility as additives and chelating agents for functional fluids, preferably mineral oil compositions and systems including automatic transmission fluids, lubricating oils and synthetic lubricants.

2. Description of the Prior Art

Lubricant additives derived from a reaction with tris-(hydroxymethyl) aminomethane (THAM) are well known and include U.S. Pat. Nos: 3,756,743; 3,632,511; 3,679,428; and 4,049,564 and United Kingdom Specification Nos: 809,001 and 984,409.

In British Pat. No. 564,506, the condensation product of THAM and formaldehyde, i.e. 1-aza-3,7-dioxybicyclo[3.3.0]oct-5-yl-methyl alcohols is said to react with fatty acids to give unstable ester products which are useful as drying oils.

U.S. Pat. No. 3,738,992 discusses esters of 1-aza-3,7-dioxabicyclo[3.3.0]oct-5-yl-methyl alcohol as antifoam agents and lubricant additives, especially for aqueous textile lubricants.

U.S. Pat. No. 3,843,726 teaches that azadioxabicyclooctane compounds, e.g. 1-aza-5-hydroxymethyl-2,8-diphenyl-3,7-dioxabicyclo(3.3.0)octane [see Example 1], (prepared by reaction of THAM and an aldehyde) can be halogenated to provide an intermediate useful for the preparation of an anti-radiation drug.

Bicyclic oxazolidines are disclosed to be produced from an aldehyde and THAM in a publication entitled Chemistry and use of Aminohydroxy Compounds by Commercial Solvents Corporation, New York, N.Y.

In U.S. Pat. No. 4,017,406 carboxylate esters of aldehyde—THAM adducts are taught to have utility as additives for oleaginous compositions with activity in gasoline as rust inhibitors and carburetor detergents; in automatic transmission fluids as friction modifiers and rust inhibitors; and, in automotive, industrial and lubricating oils as sludge dispersants, rust-inhibitors, friction modifiers and copper alloy corrosion inhibitors, the particular use depending on the molecular weight of the ester.

In prime movers utilizing a functional fluid for power transmission, including hydraulic fluids and automatic transmission fluids, it is generally necessary to remove heat generated during the operation of the functional fluid. One approach involves passing said fluid through a heat exchanger utilizing copper as a structural part or in a brazing mixture joining structural parts, e.g. the automatic transmission fluid of a car is frequently controlled by a heat exchanger located in the car radiator and immersed in the radiator coolant. Operational corrosion of the copper results in mechanically catastrophic intermixing of the functional fluid and radiator coolant (ethylene glycol) and/or loss of said fluid. It is necessary to reduce the copper corrosiveness of said fluid circulating in contact with copper so as to extend the operational lifetime of the prime mover or other mechanical device employing said fluid. One approach is to incorporate a compatible anti-copper corrosion additive into said fluid.

It is an object of this invention to provide an anti-copper-corrosion additive for functional fluids, preferably for automatic transmission fluids.

SUMMARY OF THE INVENTION

It has been discovered that oil-soluble spiro-[cycloalkane] analogues of oxazolidines, preferably substituted in the 2-position, impart excellent anti-copper-corrosion activity and metal chelating activity to mineral oils and are particularly useful when added in at least a copper-corrosion reducing amount to a functional fluid, preferably a mineral oil system useful as an automatic transmission fluid (ATF) for prime movers.

The oil-soluble additives of the invention can be defined as a spiro-[cycloalkane-1,2'-(4',4' disubstituted)oxazolidine-1',3'] and characterized generally by the formula:

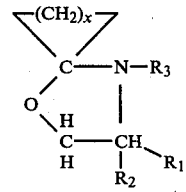

wherein: x is an integer of from 4 to 11; $R_1$ is methylol, methyl or ethyl; $R_2$ is hydrogen, methyl or ethyl; and $R_3$ is hydrogen or methyl.

The aforesaid additives of the invention are obtained from the reaction of 1 mole of a ketone having 5 to 12 carbons per mole of an aminoalkanol (includes both the monool and diol) containing from 4 to 7 carbons and preferably according to the formula:

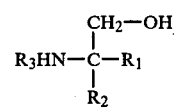

wherein $R_1$, $R_2$ and $R_3$ are the same as earlier defined. Representative compounds illustrative of said formula include: 2-amino-1,3-propanediol; 2-amino-2-methyl-1,3-propanediol; 2-(methylamino)-1,3-propanediol; 2-amino-1-propanol; and 2-amino-2-methyl-1-propanol.

Thus according to this invention there is produced a lubricating oil composition comprising a major amount of lubricating oil having dissolved therein at least a copper-corrosion reducing amount of an oil-soluble equimolar reaction product of: (a) a cycloalkanone having from 5 to 12 carbons and illustrated by cyclopentanone, cyclohexanone, cycloheptanone, cyclooctanone, cyclononanone, cyclodecanone, cycloundecanone and cyclododecanone and a 2-amino-1-alkanol having from 4 to 7 carbons and one to two hydroxy groups.

Spiro [Cycloalkane Oxazolidine]Adduct

As has been earlier noted the oil-soluble additives and/chelating agents of the invention are obtained from the reaction of one molar proportion of a cycloalkanone having 5 to 12 carbons with a 2-amino-1,3-propane diol or 2-amino-1-propanol according to the general procedures described by M. Senkus in the Journal of the American Chemical Society, 67, 1515 (1945) by E. D. Bergmann, Chemical Reviews, 53, 309 (1953) and E. M. Hancock et al. JACS, 66, 1747 (1944). It is believed the reaction occurs as follows:

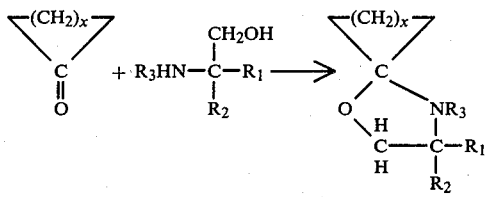

e.g. cyclopentanone + 2-amino-1,3-propane diol→spiro-[cyclopentane-1,2'-(4'-methylol)-oxazolidine-1',3'] wherein x is 4 to 11, $R_1$, $R_2$ and $R_3$ are the same as earlier defined.

The reaction is readily carried out by condensation and cyclization in a solvent such as toluene or benzene at a temperature of about 80° C. to 200° C., preferably 100° C. to 160° C., for a period until the water of condensation is removed.

The following preparations and examples are included herein as further description and illustrative of the present invention.

PREPARATION OF SPIRO-[CYCLOALKANE-1,2'-OXAZOLIDINE-1',3']

Example 1

Spiro-[cyclohexane-1,2'-(4'-methyl)-oxazolidine-1',3']. 2 moles (178 g) of 2-amino-2-methyl-1 propanol (AMP) was admixed with 2.5 moles (250 g) of cyclohexanone in a flask with a Dean Stark trap and refluxed for 2 hours at about 120° C. after which 200 cc of toluene were added. 36 ml of water were removed from the trap. The reactants were heated to 150° C. to remove some of the solvent and then vacuum distilled. The product was a clear amber oil and analyzed for 71.4%C, 11.3%H and 8.2%N.

Example 2

Spiro-[cyclohexane-1,2'-(4'-methylol-4'-ethyl)-oxazolidine-1',3']. The procedure of Example 1 was followed except that 2 moles (196 g) of cyclohexanone was used, the AMP was replaced by 1 mole (119 g) of 2-amino-2-ethyl-1,3-propane diol (AEPD), and the toluene system was heated at 137° C. until 16 ml of water were collected.

The product was a clear amber oil and analyzed for 66.2%C, 10.8%H and 7.2%N.

Example 3

Spiro-[cyclohexane-1,2'-(4'-methyl-4'-methylol)-oxazolidine-1',3'].

The procedure of Example 1 was followed except that 2 moles (196 g) of cyclohexanone was used, the AMP was replaced by 1 mole (105 g) of 2-amino-2-methyl-1,3-propane diol (AMPD) and the toluene system were heated at 135° C. until 16 cc of water were collected.

The product analyzed for 64.7%C, 10.3%H and 8.04%N.

The oil-soluble additives of this invention can be incorporated into a wide variety of functional fluids. They are preferably used in lubricating oil compositions, such as automotive crankcase lubricating oils, automatic transmission fluids, etc., and at concentrations generally within the range of about 0.01 to 1%, preferably 0.05 to 0.5 weight percent, of the total composition. Other functional fluids to which the additives can be added include not only mineral oil based fluids, but also fluids based on: lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; and mixtures of mineral oil and synthetic oil in any proportion, etc.

When the oil-soluble additives of this invention are used as anti-cooper-corrosion additives for automatic transmission fluids (ATF), it has been found that these additives do not deteriorate the frictional properties of the ATF i.e. these additives are compatible in ATF. The ATF lubricants contain many other additives which are typically blended into the lubricating mineral oil at the following range of treating levels.

| Components | Concentration range, vol. % |
|---|---|
| V.I. Improver | 1–15 |
| Metal Corrosion inhibitor (includes Cu) | 0.01–1 |
| Oxidation inhibitor | 0.01–1 |
| Dispersant | 0.5–10 |
| Pour Point Depressant | 0.01–1 |
| De-emulsifier | 0.001–0.1 |
| Anti-foaming agent | 0.001–0.1 |
| Anti-wear agent | 0.001–1 |
| Seal swellant | 0.1–5 |
| Frictional Modifier | 0.01–1 |
| Mineral Oil | Balance |

The following data is illustrative of the copper corrosion inhibition improvement of ATF lubricants afforded according to this invention.

Two commercial ATF lubricants I and II were examined in the following copper corrosion test in both modified and unmodified form. The copper corrosion test is carried out as follows: A copper specimen $3 \times \frac{1}{2} \times 1/16$ inches is polished until clean and uniform, washed in hexane, dried and weighed to the tenth of a milligram. 40 cc of the test fluid is placed in a test tube into which the copper bar is immersed, and the test tube thereafter corked with a cork with two $\frac{1}{8}$ inch holes in it. The tube is placed in a 300° F. aluminum block for 65 hours. At the end of the time, the specimen is removed, washed in hexane, rubbed vigorously with a paper towel to remove any loose deposits, rewashed and reweighed.

TABLE II

| Copper Corrosion Tests, mg. lost in 65 hours | | |
|---|---|---|
| ATF Lubricant | ATF I | ATF II |
| Unmodified | 15.5 | 27.7 |
| Modified by addition of 0.26 wt. % of Product of Example 3 | 4.2 | 10.9 |

The additives of this invention were discovered to have chelation activity for metals as evidenced by the roto-evaporation of an equimolar mixture of copper oleate and the product of Example 2 which yielded a product characterized by the absence of infrared absorption in the 3400 to 3600 cm$^{-1}$ range, i.e. the range where OH-NH absorption obtains. The lack of said absorption confirms the presence of chelated structures.

It has also been found that the additives of the invention show anti-oxidant properties when added to a No. 2 heating oil, i.e., when 66 ppm of the product of Example 3 was added to heating oil subjected to 265° F. with an air injection for a period of 6 hours, the sediment level dropped from 1.16 mg to 0.70 mg. Therefore, the additives of the invention are useful when present in an amount of 30–80 ppm in middle distillate fuels to provide for a marked reduction of the oxidation of said middle distillates when subjected to normal environments.

It has also been found that when the additives of this invention are reacted with an equimolar amount of octadecenyl succinic anhydride, the resulting product can be added to an automatic transmission fluid at a concentration of from 0.01–0.5, preferably about 0.225 volume percent to enhance the lubricity, i.e. improve the friction modification properties, of a lubricating oil. Thus, it is desirable to modify lubricating oils by the addition of the reaction product of a $C_8$–$C_{30}$ dibasic acid, preferably a $C_{12}$–$C_{18}$ substituted succinic acid material, for example, succinic anhydride with the additives of the invention, for example, the equimolar reaction product of the product of Example 3 with octadecenyl succinic anhydride.

The invention in its broader aspect is not limited to the specific details shown and described and departures may be made from such details without departing from the principles of the invention and without sacrificing its chief advantages.

What is claimed is:

1. A composition comprising a major amount of a mineral oil functional fluid and a minor but at least a copper-corrosion inhibiting amount of an oil-soluble spiro-(cycloalkane-oxazolidine) characterized by the formula:

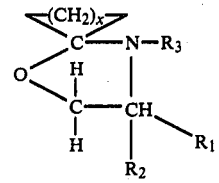

wherein: x is an integer of from 4 to 11; $R_1$ is methylol, methyl or ethyl; $R_2$ is hydrogen, methyl or ethyl; and $R_3$ is hydrogen or methyl.

2. A composition according to claim 1 wherein said functional fluid is a mineral oil base automatic transmission fluid.

3. A composition according to claim 2 wherein said spiro-[cycloalkane-oxazolidine] is obtained from the equimolar reaction of an amino-alkanol having one or two hydroxy groups and 4 to 7 carbons with a cycloalkanone having from 5 to 12 carbons.

4. A composition according to claim 2 wherein said spiro-[cycloalkane-oxazolidine] is spiro-[cyclohexane-1,2'-(4'-methyl)-oxazolidine-1',3'] present in an amount ranging from 0.01 to 1 weight percent based on the total weight of said composition.

5. A composition according to claim 2 wherein said spiro-[cycloalkane-oxazolidine] is spiro-[cyclohexane-1,2'-(4'-methyl-4'-ethyl)-oxazolidine-1',3'] present in an amount ranging from 0.01 to 1 weight percent based on the total weight of said composition.

6. A composition according to claim 2 wherein said spiro-[cycloalkane-oxazolidine] is spiro-[cyclohexane-1,2'-(4'-methyl-4'-methylol)-oxazolidine,-1',3'] present in an amount ranging from 0.01 to 1 weight percent based on the total weight of said composition.

* * * * *